United States Patent [19]

Salem et al.

[11] Patent Number: 5,306,858
[45] Date of Patent: Apr. 26, 1994

[54] OXIDIZING PARAFFIN HYDROCARBONS

[75] Inventors: George F. Salem; Charles J. Besecker, both of Cleveland Heights; Susan M. Kenzig; Walter J. Kowlaski, both of Valley View; Larry M. Cirjak, Burton, all of Ohio

[73] Assignee: The Standard Oil Company, Cleveland, Ohio

[21] Appl. No.: 979,035

[22] Filed: Nov. 20, 1992

[51] Int. Cl.$^5$ ............................................. C07C 5/327
[52] U.S. Cl. .................................. 585/658; 585/654; 585/656; 585/661
[58] Field of Search ................ 585/654, 656, 658, 661

[56] References Cited

U.S. PATENT DOCUMENTS

| | | | |
|---|---|---|---|
| 3,385,796 | 5/1968 | Kerr | 502/209 |
| 4,043,943 | 8/1977 | Schreider | 502/209 |
| 4,064,070 | 12/1977 | Harrison | 502/209 |
| 4,294,722 | 10/1981 | Bremer et al. | 502/209 |
| 4,644,089 | 2/1987 | Lee | 585/661 |

FOREIGN PATENT DOCUMENTS 0158976 10/1985 European Pat. Off. .

OTHER PUBLICATIONS

Montes et al., "Isolated Rexox Centers within Microporous Environments 2. Vanadium Containing Aluminophosphate Molecular Sieve Five" J. Phys. Chem. vol. 94, pp. 6431–6435 (1990).

Centi et al., "Physicochemical Characterization of V-Silicalite", J. Phys. Chem., vol. 96, pp. 2617–2629, (1992).

*Primary Examiner*—Patrick P. Garvin
*Assistant Examiner*—E. D. Irzinski
*Attorney, Agent, or Firm*—Charles S. Lynch; Michael F. Esposito; David J. Untener

[57] ABSTRACT

Disclosed is a process for oxidizing a paraffin hydrocarbon containing 2 to 5 carbon atoms and no quaternary carbon atom to an olefin having the same number of carbon atoms as said paraffin by contacting said paraffin in a reaction zone with molecular oxygen and a VAPO-5 microporous molecular sieve as catalyst.

20 Claims, No Drawings

OXIDIZING PARAFFIN HYDROCARBONS

This invention relates to the oxidation of paraffin hydrocarbons containing 2 to 5 carbon atoms to monoolefins in the presence of a microporous vanadoaluminophosphate molecular sieve. The type of molecular sieve employed is known as a VAPO-5 molecular sieve.

VAPO-5 and AlPO-5 microporous molecular sieves have been broadly disclosed as members of a family of FCAPO molecular sieves that are possibly useful in hydrocarbon conversion and oxidative combustion reactions, including cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization, in European Patent Application 85104386.9, filed Apr. 11, 1985, published as 0158976 on Oct. 23, 1985. This same application suggests such FCAPO molecular sieves used as a catalyst, or with a co-catalyst or promoter; or modified to promote a myriad other reactions. However, there is no suggestion in this published European application to employ such a microporous molecular sieve of the VAPO-5 type to catalyze the oxidation of a paraffin to an olefin in the presence of molecular oxygen as oxidant.

Such a reaction so catalyzed is unsuggested in any literature known to the present application. While not understanding the mechanism, it is believed that the presence of vanadium in the V-O-P r V-O-Al form is responsible for the power of the VAPO-5 catalysts used in our invention to convert a paraffin to an olefin at high selectivity without runaway combustion of paraffin to form carbon oxides and water. Since the alkane substrates all easily fit within the pores of the microporous molecular sieve, we are not using the sieving or shape-selective property of the catalyst.

In any event, it is an object of our invention to provide a new process to oxidize a paraffin to an olefin in the presence of a catalyst which is new for such reaction.

Other objects, as well as other aspects, features and advantages of the invention will be pointed out herein or will become apparent from a study of the accompanying disclosure and the claims.

The foregoing and other objects are achieved by the present invention according to one aspect of which there is provided a process for oxidizing a paraffin hydrocarbon containing 2 to 5, especially 3 to 4, carbon atoms and no quaternary carbon atom to an olefin hydrocarbon having the same number of carbon atoms as said paraffin by contacting said paraffin in a reaction zone with molecular oxygen as oxidant and a VAPO-5 microporous molecular sieve as catalyst.

In another aspect of the present invention the foregoing process of the invention includes adding $NH_3$ in the feed to the process. This expedient greatly increases the selectivity and yield to propylene and the conversion of propane while not increasing selectivity to carbon oxides. In this connection attention is invited to U.S. Pat. No. 5,094,989 which teaches that an oxidic vanadium- and antimony-containing catalyst treated with certain alcohols including isobutanol is activated, compared to untreated catalyst, when used in the vapor phase ammoxidation of propane to make acrylonitrile or acrylonitrile plus propylene. This reference is not believed to make obvious in any way the use of $NH_3$ to treat the present catalysts to be used in our process. Reference is made to the discussion of Example 5 later on in this application.

In still another aspect of the present invention the basic process of the invention includes the step of treating the calcined catalyst with an aqueous solution of ammonium acetate. This procedure allows the use of higher temperatures in oxidizing propane while increasing the yield. In this connection attention is invited to the article by Centi et al. in *The Journal of Physical Chemistry*, Vol. 96, No. 6, 1992 in which it is said that the polynuclear vanadium oxide species can be removed from V-silicalite zeolites by ammonium acetate extraction. This reference is background and obviously does not bear on the patentability of any claim herein, but it does disclose the use of such zeolites as catalysts in the /xidative dehydrogenation of alkanes. No FCAPO or VAPO-5 molecular sieves are disclosed.

For the sake of completeness it is noted that a body of patent art exists on the use of certain oxygenated hydrocarbons, including alcohols such as isobutanol, to adjust the valence state of the vanadium in a vanadium-oxygen-phosphorus compound or to act as a reaction medium in the reaction of the vanadium compound and the phosphorus compound, or both, in making or activating catalysts used in the oxidation of alkanes, alkenes or even butadiene, to make maleic anhydride. In this general category are Bremer et al. U.S. Pat. No. 4,294,722; Schneider U.S. Pat. No. 4,043,943 and Harrison U.S. Pat. No. 4,064,070. U.S. Pat. No. 3,385,796 discloses reacting a vanadium compound, a phosphorus compound and a copper compound in a suitable reducing solvent which can be an alcohol. This can be carried out with the carrier, 7hich can be alumina, present in all steps. After heating in the presence of an oxidizing gas, the catalyst is more active. However, these catalysts are not molecular sieves, and it is not obvious that our use of alcohols such as isobutanol in post treatment of our catalyst as in the preparation of the catalyst for use in our Example 4 affects the valence of any of the vanadium in the catalyst; indeed, it is not known whether the isobutanol has this effect. Nor is it known whether this isobutanol post treatment has the effect of washing out any vanadium compound.

One suitable method of preparing the VAPO-5 microporous molecular sieve catalysts used in the process is shown in the specific examples of catalyst preparation, using the Montes et al. method cited infra.

In such method we usually use a starting synthesis reaction mixture having the gross empirical molar relationship:

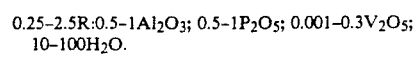
0.25–2.5R:0.5–1Al$_2$O$_3$; 0.5–1P$_2$O$_5$; 0.001–0.3V$_2$O$_5$; 10–100H$_2$O.

More usually this empirical formula is in a narrower range, as follows:

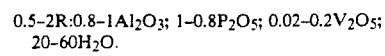
0.5–2R:0.8–1Al$_2$O$_3$; 1–0.8P$_2$O$_5$; 0.02–0.2V$_2$O$_5$; 20–60H$_2$O.

In most of our current work this empirical formula has been restricted still further, as follows:

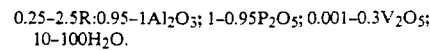
0.25–2.5R:0.95–1Al$_2$O$_3$; 1–0.95P$_2$O$_5$; 0.001–0.3V$_2$O$_5$; 10–100H$_2$O.

In the foregoing formulas, R is the organic template that will result in a VAPO-5 type microporous molecular sieve. We used tripropyl amine, but many other such templates are well known and can be used to make a VAPO-5 material for use in our oxidation process.

The foregoing conventional designation of $Al_2O_3$, $P_2O_5$ and $V_2O_5$ does not mean that the elements are added in this form, but merely that the form added was equivalent to the stated mols of $Al_2O_3$, $P_2O_5$ or $V_2O_5$ as the case may be. We usually add Al oxide as pseudoboemite having the empirical formula AlO(OH); phosphorus oxide as phosphoric acid and vanadium oxide as $V_2O_5$ or $V_2O_3$.

In making the VAPO-5 microporous molecular sieve catalyst precursors we used the method described in C. Montes, M. Davis, B. Murray, and M. Narayama, *Journal of Physical Chemistry*, Vol. 94, No. 6431, 1990; the entire contents of which is incorporated by reference.

The catalyst precursor for Examples 1 and 2 in Table 1 was made as follows: solution 1 containing 17.0 g of 85 weight percent phosphoric acid, that was then diluted with 12 g of $H_2O$, was made. A slurry of 10.6 g of pseudoboemite, having the empirical formula AlO(OH), and 33.8 g of $H_2O$ was prepared and stirred for 10 minutes. Solution 1 was added to the stirring slurry and a white viscous gel was formed and aged by being stirred at ambient conditions for 90 minutes. Next, 0.7 g of $V_2O_5$ was added to the stirring gel and the color changed to yellow. After being homogenized for 20 minutes, 30 mL of tripropylamine ($Pr_3N$) was added. The entire gel was then homogenized further for 90 minutes, giving a final gel composition of $Pr_3N.Al_2O_3.0.95P_2O_5.0.05V_2O_5.40H_2O$ and a pH of 6.9. The gel was heated in a Teflon-lined autoclave to 150° C. at autogenous pressure and held at that temperature for 5 days. The autoclave was then quenched in cold water. The contents of the autoclave were slurried in water, stirred for several minutes and then the solids were allowed to settle and the supernatent liquid discarded. This procedure was repeated several times until a clear liquid was obtained. Then, the solid was filtered and dried at room temperature, and then dried by heating in air in an oven at 150° C. for about 16 hours. X-ray powder diffraction data was obtained and confirmed that the VAPO-5 precursor crystals were obtained, giving the pattern reported for pure crystals in the C. Montes publication referenced earlier. To make the final microporous molecular sieve the dried crystal powder was calcined in air at 350° C. for 4 hours to remove the template amine and then at 550° C. for about 16 additional hours. 8 g of this material was slurried with 13.3 g of Ludox ® colloidal silica HS-40 of E. I. du Pont de Nemours. This material containing 40 weight percent silica (as $SiO_2$) and stabilized with 0.41 weight percent titratable alkali (as $Na_2O$), when mixed with the calcined catalyst made a thick paste, which was calcined in air for 16 hours at 550° C. The final catalyst was obtained by mild grinding and sieving to 30-45 mesh size. A portion of this catalyst was also used in Example 2.

The catalyst precursors and catalysts for Examples 3 and 5 were as in Example 1, except that 1.4 g of $V_2O_5$ was used instead of 0.7 g. In other words the initial loading of V was double that of Examples 1 and 2.

The catalyst of Example 4 was the same as the catalyst used for Example 3, except that the catalyst was post-treated as follows: 8 g of the catalyst was refluxed overnight in 400 ml of isobutanol, filtered, washed three times with 500 ml of water and then dried at 110° C. for 60 hours. This was done in a step just prior to the step of slurrying with the 40 percent colloidal silica.

The catalyst precursor of Example 6 had the same initial loading of V as that of Example 1.

The precursor of Example 6 was made as follows: solution 1 containing 17.0 g of 85 weight percent phosphoric acid, that was then diluted with 12 g of $H_2O$ was made. A slurry of 10.6 g of pseudoboemite, having the empirical formula AlO(OH), and 33.8 g of $H_2O$ was prepared and stirred for 10 minutes. Solution 1 was added to the stirring slurry and a white viscous gel was formed and aged by being stirred at ambient conditions for 90 minutes. Next, 0.7 g of $V_2O_5$ was added to the stirring gel and the color changed to yellow. After being homogenized for 20 minutes, 30 mL of tripropylamine ($Pr_3N$) was added. The entire gel was then homogenized further for 90 minutes, giving a final gel composition of $Pr_3N.Al_2O_3.0.95P_2O_5.0.05V_2O_5.40H_2O$ and a pH of 6.9. The gel was heated in a Teflon-lined autoclave to 150° C. at autogenous pressure and held at that temperature for 5 days. The autoclave was then quenched in cold water. The contents of the autoclave were slurried in water, stirred for several minutes and then the solids were allowed to settle and the supernatent liquid discarded. This procedure was repeated several times until a clear liquid was obtained. Then, the solid was filtered and dried at room temperature, and then dried by heating in air in an oven at 150° C. for about 16 hours. X-ray powder diffraction data was obtained and confirmed that the VAPO-5 precursor crystals were obtained, giving the pattern reported for pure crystals in the C. Montes publication referenced earlier. To make the final microporous molecular sieve the dried crystal powder was calcined in air at 350° C. for 4 hours to remove the template amine and then at 550° C. for about 16 additional hours. 6.5 g of this material was treated with $NH_4OAc$ by adding the 6.5 g to a solution of 148 gms of ammonium acetate in 100 ml of water. The mixture was stirred at ambient temperature for 30 minutes. The solid was isolated by filtration and washed with 400 ml of water. It was then calcined at 550° C. in air for 16 hours. This calcined solid was slurried with 10.8 g of Ludox ® colloidal silica HS-40 of E. I. du Pont de Nemours. This material containing 40 weight percent silica (as $SiO_2$) and stabilized with 0.41 weight percent titratable alkali (as $Na_2O$), when mixed with the calcined catalyst made a thick paste, which was calcined in air for 16 hours at 550° C. The final catalyst was obtained by mild grinding and sieving to 30-45 mesh size.

The catalyst precursor for Example 7 in Table 1 was made as follows: solution 1 containing 17.0 g of 85 weight percent phosphoric acid, that was then diluted with 12 g of $H_2O$ was made. A slurry of 10.6 g of pseudoboemite, having the empirical formula AlO(OH), and 33.8 g of $H_2O$ was prepared and stirred for 10 minutes. Solution 1 was added to the stirring slurry and a white viscous gel was formed and aged by being stirred at ambient conditions for 90 minutes. Next, 0.7 g of $V_2O_5$ was added to the stirring gel and the color changed to yellow. After being homogenized for 20 minutes, 30 mL of tripropylamine ($Pr_3N$) was added. The entire gel was then homogenized further for 90 minutes, giving a final gel composition of $Pr_3N.P_2O_5.0.95Al_2O_3.0.05V_2O_5.40H_2O$. The gel was heated in a Teflon-lined autoclave to 150° C. at autogenous pressure and held at that temperature for 5 days. The autoclave was then quenched in cold water. The contents of the autoclave were slurried in water, stirred for several minutes and then the solids were allowed to settle and the supernatent liquid discarded. This procedure was repeated several times until a clear liquid was obtained. Then, the solid was filtered and dried at room temperature, and then dried by heating in air in an oven at 150° C. for about 16 hours. X-ray powder diffraction data was obtained and confirmed that the VAPO-5 precursor crystals were obtained, giving the pattern reported for pure crystals in the C. Montes publication referenced earlier. To make the final microporous molecular sieve the dried crystal powder was calcined in air at 350° C. for 4 hours to remove the template amine and then at 550° C. for about 16 additional hours. 2.3 g of this material was slurried with 4.69 g of Ludox ® colloidal silica HS-40 of E. I. du Pont de Nemours. This material containing 40 weight percent silica (as $SiO_2$) and stabilized with 0.41 weight percent titratable alkali (as $Na_2O$), when mixed with the calcined catalyst made a thick paste, which was calcined in air for 16 hours at 550° C. The final catalyst was obtained by mild grinding and sieving to 30–45 mesh size.

The catalyst for Example 8 in Table 2 was prepared exactly as was the catalyst for Example 7.

The catalyst precursor for Example 9 in Table 3 was made as follows: solution 1 containing 8.5 g of 85 weight percent phosphoric acid, that was then diluted with 6 g of $H_2O$ was made. A slurry of 5.3 g of pseudoboemite, having the empirical formula AlO(OH), and 16.9 g of $H_2O$ was prepared and stirred for 10 minutes. Solution 1 was added to the stirring slurry and a white viscous gel was formed and aged by being stirred at ambient conditions for 90 minutes. Next, 0.29 g of $V_2O_3$ was added to the stirring and the color changed to yellow. After being homogenized for 20 minutes, 15 mL of tripropylamine ($Pr_3N$) was added. The entire gel was then homogenized further for 90 minutes, giving a final gel composition of $Pr_3N.Al_2O_3.0.95P_2O_5.0.29V_2O_3.40H_2O$. The gel was heated in a Teflon-lined autoclave to 150° C. at autogenous pressure and held at that temperature for 5 days. The autoclave was then quenched in cold water. The contents of the autoclave were slurried in water, stirred for several minutes and then the solids were allowed to settle and the supernatent liquid discarded. This procedure was repeated several times until a clear liquid was obtained. Then, the solid was filtered and dried at room temperature, and then dried by heating in air in an oven at 150° C. for about 16 hours. X-ray powder diffraction data was obtained and confirmed that the VAPO-5 precursor crystals were obtained, giving the pattern reported for pure crystals in the C. Montes publication, referenced earlier. To make the final microporous molecular sieve the dried crystal powder was calcined in air at 350° C. for 4 hours to remove the template amine and then at 550° C. for about 16 additional hours. 4 g of this material was slurried with 6.7 g of Ludox ® colloidal silica HS-40 of E. I. du Pont de Nemours. This material containing 40 weight percent silica (as $SiO_2$) and stabilized with 0.41 weight percent titratable alkali (as $Na_2O$), when mixed with the calcined catalyst made a thick paste, which was calcined in air for 16 hours at 550° C. The final catalyst was obtained by mild grinding and sieving to 30–45 mesh size.

All of the oxidation runs in the specific examples in this application, including Examples 1–9 of Tables 1, 2 and 3, were effected by passing the gaseous feed stream downflow through a 20 cc stainless steel tubular fixed bed reactor containing 3 cc of 30–40 mesh catalyst, diluted to 13 cc with 3 mm glass beads, with 5 cc of glass beads at the top and 2 cc of glass beads at the bottom. The gaseous effluent was passed through an aqueous acid solution to scrub out trace contaminants, and the products were analyzed by gas chromatographic analysis.

The specific examples of oxidation of paraffins to olefins set forth herein are representative only, and are not to be considered as limiting.

Referring to the oxidation examples summarized in Table 1, the catalyst and feed ratios in Examples 1 and 2 are the same; the lower temperature of Example 2 results in a lower conversion of propane and a lower yield of propylene but a somewhat better selectivity to propylene. A heat savings is also realized at the lower 450° C. temperature.

In Example 3 the temperature of 450° is the same as Example 2, but the catalyst used had twice the vanadium loading, giving a higher yield of propylene, higher conversion of propane, a higher selectivity to propylene and a lower selectivity to CO plus $CO_2$.

TABLE 1

| Mol Feed Ratios $C_3/O_2/N_2/He$ | Example | Temperature, °C. | Contact Time, Secs | Percent $C_3$(1) Conversion | Selectivities, % | | | Percent yield of Propene |
|---|---|---|---|---|---|---|---|---|
| | | | | | Propene | CO | $CO_2$ | |
| 12.0/5.2/7.8/75.0 | 1 | 500 | 0.76 | 16.9 | 68.3 | 20.3 | 11.4 | 11.5 |
| 12.0/5.2/7.8/75.0 | 2 | 450 | 0.82 | 5.6 | 69.7 | 17.5 | 12.8 | 3.9 |
| 11.5/5.1/7.6/76.0(4) | 3 | 450 | 0.87 | 11.8 | 74.4 | 14.5 | 11.2 | 8.8 |
| 11.3/5.4/7.0/76.3 | 4 | 450 | 0.82 | 17.1 | 64.8 | 22.5 | 12.6 | 11.1 |
| 11.4/5.2/7.3/76.1(2)(3) | 5 | 450 | 0.80 | 14.1 | 80.2 | 11.3 | 8.5 | 11.3 |
| 9.6/10.9/13.5/65.9 | 6 | 520 | 0.66 | 24.4 | 48.7 | 29.6 | 21.7 | 12.8 |
| 11.5/4.9/8.0/75.6 | 7 | 480 | 0.78 | 15.8 | 80.1 | 12.8 | 7.3 | 12.6 |

(1)$C_3$ is propane.
(2)gaseous feed contained 0.19 mols $NH_3$ per mol of $C_3$.
(3)WWH (weight of propane fed/unit weight of catalyst/Hr.) was 0.60.
(4)WWH was 0.63.

TABLE 2

| Mol Feed Ratios (1) i-$C_4/O_2/N_2/He$ | Example | Temperature, °C. | Contact Time, Secs | Percent isobutane Conversion | Selectivities, %(2) | | | Percent yield of isobutene |
|---|---|---|---|---|---|---|---|---|
| | | | | | isobutene | CO | $CO_2$ | |
| 13.3/13.8/5.3/67.6 | 8 | 480 | 0.68 | 15.6 | 40.6 | 27.8 | 19.2 | 6.3 |

(1) i-$C_4$ is isobutane.
(2)combined cis and trans 2-butenes were less than 0.5% selectivity.

TABLE 3

| Mol Feed Ratios (1) $C_4/O_2/N_2/He$ | Example | Temperature, °C. | Contact Time, Secs | Percent n-butane Conversion | Selectivities, %(2) | | | Percent yield of 1-butene |
| --- | --- | --- | --- | --- | --- | --- | --- | --- |
| | | | | | 1-butene | CO | $CO_2$ | |
| 13.0/26.1/60.9/0 | 9 | 500 | 0.34 | 50.3 | 28.3 | 38.9 | 22.2 | 14.2 |

(1) $C_4$ is n-butane.
(2) Selectivity to propene, 5.6%; to ethene, 2.5%; to combined cis and trans 2-butene and ethane, <1%.

When the same catalyst used in Example 3 as was used in Example 4 was treated with isobutanol and used at the same temperature and as close to the same WWH as possible, the yield of propylene increased, but at the expense of a greater selectivity of carbon oxides. Note also that results are also comparable to Example 1 but at a heat-saving 50° C. lower reaction temperature.

When in Example 5, the same catalyst as Example 3 is used but with $NH_3$ in the feed, the selectivity of propane conversion to propylene was greatly increased, while the selectivity of conversion of propane to carbon oxides was very significantly reduced.

In Example 6 in which the catalyst used was treated with ammonium acetate it is demonstrated that a higher yield of propylene can be realized at a higher reaction temperature.

Example 7 shows that a different Al:P ratio in the catalyst increased the yield compared to Example 1 at a lower reaction temperature, and with lower selectivity to carbon oxides.

EXAMPLE 10

When repeating Example 3, except substituting n-pentane for propane, pentane is converted to a mixture of substantially mono-pentenes, CO and $CO_2$. Some butenes, propylene and ethylene are made in small amounts.

As will be evident to those skilled in the art, various modifications of this invention can be made or followed in the light of the foregoing disclosure and discussion without departing from the spirit and scope of the disclosure or from the scope of the claims.

What we claim is:

1. A process for oxidizing a paraffin hydrocarbon containing 2 to 5 carbon atoms and no quaternary carbon atom to an olefin having the same number of carbon atoms as said paraffin by contacting said paraffin in a reaction zone with molecular oxygen and a VAPO-5 microporous molecular sieve as catalyst under conditions sufficient to effect the recited oxidizing reaction.

2. A process of claim 1 wherein said paraffin has 3 to 4 carbon atoms.

3. A process of claim 1 wherein said paraffin is propane.

4. A process of claim 1 wherein said paraffin is n-butane.

5. A process of claim 1 wherein said paraffin is isobutane.

6. A process of claim 1 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.25-2.5R:0.5-1Al_2O_3; 0.5-1P_2O_5; 0.001-0.3V_2O_5; 10-100H_2O$, and wherein R is the organic template.

7. A process of claim 1 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.5-2R:0.8-1Al_2O_3; 1-0.8P_2O_5; 0.02-0.2V_2O_5; 20-60H_2O$, and wherein R is the organic template.

8. A process of claim 1 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.25-2.5R:0.95-1Al_2O_3; 1-0.95P_2O_5; 0.001-0.3V_2O_5; 10-100H_2O$, and wherein R is the organic template.

9. A process of claim 2 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.25-2.5R:0.5-1Al_2O_3; 0.5-1P_2O_5; 0.001-0.3V_2O_5; 10-100H_2O$, and wherein R is the organic template.

10. A process of claim 2 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.5-2R:0.8-1Al_2O_3; 1-0.8P_2O_5; 0.02-0.2V_2O_5; 20-60H_2O$, and wherein R is the organic template.

11. A process of claim 2 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.25-2.5R:0.95-1Al_2O_3; 1-0.95P_2O_5; 0.001-0.3V_2O_5; 10-100H_2O$, and wherein R is the organic template.

12. A process of claim 3 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $0.25-2.5R:0.5-1Al_2O_3; 0.5-1P_2O_5; 0.001-0.3V_2O_5; 10-100H_2O$, and wherein R is the organic template.

13. A process of claim 3 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.5-2R:0.8-1Al_2O_3; 1-0.8P_2O_5; 0.02-0.2V_2O_5; 20-60H_2O,$$

and wherein R is the organic template.

14. A process of claim 3 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.25-2.5R:0.95-1Al_2O_3; 1-0.95P_2O_5; 0.001-0.3V_2O_5; 10-100H_2O,$$

and wherein R is the organic template.

15. A process of claim 4 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.25-2.5R:0.5-1Al_2O_3; 0.5-1P_2O_5; 0.001-0.3V_2O_5; 10-100H_2O.$$

and wherein R is the organic template.

16. A process of claim 4 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.5-2R:0.8-1Al_2O_3; 1-0.8P_2O_5; 0.02-0.2V_2O_5; 20-60H_2O.$$

and wherein R is the organic template.

17. A process of claim 4 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.25-2.5R:0.95-1Al_2O_3; 1-0.95P_2O_5; 0.001-0.3V_2O_5; 10-100H_2O,$$

and wherein R is the organic template.

18. A process of claim 5 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.25-2.5R:0.5-1Al_2O_3; 0.5-1P_2O_5; 0.001-0.3V_2O_5; 10-100H_2O,$$

and wherein R is the organic template.

19. A process of claim 5 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.5-2R:0.8-1Al_2O_3; 1-0.8P_2O_5; 0.02-0.2V_2O_5; 20-60H_2O.$$

and wherein R is the organic template.

20. A process of claim 5 wherein the VAPO-5 microporous molecular sieve catalyst is made from a synthesis reaction mixture having an organic template and Al, P and V (expressed as $Al_2O_3$, $P_2O_5$ and $V_2O_5$) and water, all in the proportions indicated by the empirical formula, $$0.25-2.5R:0.95-1Al_2O_3; 1-0.95P_2O_5; 0.001-0.3V_2O_5; 10-100H_2O.$$

and wherein R is the organic template.

* * * * *